(12) United States Patent
Boots

(10) Patent No.: US 8,273,710 B2
(45) Date of Patent: *Sep. 25, 2012

(54) PROTEIN HYDROLYSATE ENRICHED IN PEPTIDES INHIBITING DPP-IV AND THEIR USE

(75) Inventor: Jan-Willem Pieter Boots, Bilthoven (NL)

(73) Assignee: Campina Nederland Holding B.V., Zaltbommel (NL)

( * ) Notice: Subject to any disclaimer, the term of this patent is extended or adjusted under 35 U.S.C. 154(b) by 354 days.

This patent is subject to a terminal disclaimer.

(21) Appl. No.: 11/722,667

(22) PCT Filed: Nov. 30, 2005

(86) PCT No.: PCT/NL2005/050056
§ 371 (c)(1),
(2), (4) Date: Jun. 13, 2008

(87) PCT Pub. No.: WO2006/068480
PCT Pub. Date: Jun. 29, 2006

(65) Prior Publication Data
US 2009/0075904 A1    Mar. 19, 2009

(30) Foreign Application Priority Data
Dec. 23, 2004    (EP) .................................... 04078502

(51) Int. Cl.
*A61K 38/00* (2006.01)
*A61K 38/08* (2006.01)
(52) U.S. Cl. .......... 514/4.8; 514/5.7; 514/6.9; 514/16.6; 514/17.9; 514/21.7
(58) Field of Classification Search .................. None
See application file for complete search history.

(56) References Cited

U.S. PATENT DOCUMENTS

| | | | |
|---|---|---|---|
| 5,405,637 A | 4/1995 | Martinez et al. | |
| 5,681,586 A | 10/1997 | Gordon | |
| 7,053,055 B2 | 5/2006 | Demuth et al. | |
| 2002/0182301 A1 | 12/2002 | Draaisma et al. | |
| 2004/0151738 A1 | 8/2004 | Oriol et al. | |
| 2004/0152745 A1 | 8/2004 | Jackson et al. | |
| 2004/0259919 A1* | 12/2004 | Magnin et al. ................. | 514/357 |

FOREIGN PATENT DOCUMENTS

| | | |
|---|---|---|
| DE | 42 11 878 A1 | 10/1993 |
| EP | 1 201 137 A1 | 5/2002 |
| EP | 1 367 065 A1 | 12/2003 |
| EP | 1 422 293 A1 | 5/2004 |
| JP | 04-264098 A | 9/1992 |
| JP | 08-099994 A | 4/1996 |
| JP | 2002-284668 A | 10/2002 |
| WO | WO 94/11689 * | 5/1994 |
| WO | WO 98/02165 A1 | 1/1998 |
| WO | WO 00/54603 | 9/2000 |
| WO | WO 01/37850 A2 | 5/2001 |
| WO | WO-02/13850 A1 | 2/2002 |
| WO | WO-02/45523 A2 | 6/2002 |
| WO | WO 02/094038 A1 | 11/2002 |
| WO | WO-03/002593 A2 | 1/2003 |
| WO | WO-03/035051 A2 | 5/2003 |
| WO | WO 03/074129 A1 | 9/2003 |
| WO | WO-03/102195 A1 | 12/2003 |
| WO | WO 03/105882 A1 | 12/2003 |
| WO | WO 2004/002241 A1 | 1/2004 |
| WO | WO 2004/022083 A1 | 3/2004 |
| WO | WO 2004/024177 A1 | 3/2004 |
| WO | WO 2004/069265 A1 | 8/2004 |
| WO | WO-2004/098644 A1 | 11/2004 |
| WO | WO-2005/081628 A2 | 9/2005 |
| WO | WO 2005/081628 A2 | 9/2005 |
| WO | WO 2005/117933 A1 | 12/2005 |
| WO | WO-2006/005757 A2 | 1/2006 |
| WO | WO 2006/068480 A2 | 6/2006 |
| WO | WO-2007/064208 A1 | 6/2007 |

OTHER PUBLICATIONS

Van Loon et al., Plasma insulin responses after ingestion of different amino acid or protein mixtures with carbohydrate, 2000, Journal of American Society for Clinical Nutrition, Issue 72, pp. 96-105.*
Conarello, S.L. et al. 2003, "Mice Lacking dipeptidyl peptidase IV are protected against obesity and insulin resistance" Proc. Nat.Acad. Sci. USA, vol. 100:6825-6830.
Deacon, C.F. et al., 1998, "Dipeptidyl Peptidase IV Inhibition Potentiates the Insulintropic Effect of Glucagon-Like Peptide 1 in the Anesthetized Pig" Diabetes, vol. 47:764-769.
Ahren, B. et al., 2002, "Inhibition of Dipeptidyl Peptidase IV Improves Metabolic Control Over a 4-Week Study Period in Type 2 Diabetes" Diabetes Care, vol. 25:869-875.
Naslund, E. et al., 1998, "Glucagon-like peptide 1 increases the period of postprandial satiety and slows gastric emptying in obese men" Am.J.Clin. Nutr., vol. 68:525-530.
Meneilly, G.S. et al., "Effects of 3 Months of Continuous Subcutaneous Administration of Glucagon-Like Peptide 1 in Elderly Patients With Type 2 Diabetes" Diabetes Care, vol. 26: 2835-2841.
Reinhold, D. et al., 2000, "Dipeptidyl Peptidase IV (CD26): Role in T Cell Activation and Autoimmune Disease" Cellular Peptidases in Immune Functions and Diseases 2, Langner and Ansorge ed., Kluwer Academic/Plenum Publishers, 155-160.

(Continued)

*Primary Examiner* — Robert Landsman
*Assistant Examiner* — Ian Dang
(74) *Attorney, Agent, or Firm* — Gilberto M. Villacorta; Sunit Talapatra; Foley & Lardner

(57) ABSTRACT

Disclosed is a protein hydrolysate having DPP-IV inhibiting activity, the hydrolysate being enriched in peptides having a length of 2-8 amino acids comprising at least one proline residue, an isolated peptide derivable from such a protein hydrolysate, or a mixture thereof, and the use of such protein hydrolysate or isolated peptide for the manufacture of a medicament, food supplement, beverage or food product for prophylaxis and/or treatment of a DPP-IV mediated condition, in particular chosen from the group of obesity, type 2 diabetes mellitus and an immunological disorder.

10 Claims, 2 Drawing Sheets

OTHER PUBLICATIONS

Steinbrecher, A. et al., 2000, "Dipeptidyl Peptidase IV in Inflammatory CNS Disease" Cellular Peptidases in Immune Functions and Diseases 2, Langner and Ansorge ed., Kluwer Academic/Plenum Publishers, 145-153.

Tanaka S., et al., 1997, "Suppression of Arthritis by the Inhibitors of Dipeptidyl Peptidase IV" Int J. Immunopharmac, vol. 19:15-24.

Van Elswijk et al., "Rapid detection and identification of angiotensin-converting enzyme inhibitors by on-line liquid chromatography-biochemical detection, coupled to electrospray mass spectrometry" J. Chromatography, 2003, 1020:45-58.

Davy et al., "Purification and Characterization of Barley Dipeptidyl Peptidase IV" Plant Physiol (2000) 122:425-432.

International Search Report mailed Oct. 26, 2006 in International Application No. PCT/NL2005/050056, 7 pages.

Database WPI, Section Ch, Week 199245 Derwent Publications Ltd., London, GB, AN 1992-368170, JP 04-264098 A, Sep. 18, 1992 [XP002402537].

Database WPI, Section Ch, Week 200316 Derwent Publications Ltd., London, GB, AN 2003-160072, JP 2002-284668 A, Oct. 3, 2002 [XP002402536].

Database WPI, Week 199625 Derwent Publications Ltd., London, GB, AN 1996-246958, JP 08-099994 A, Apr. 16, 1996 [XP002402538].

Lange et al., "Global expression profiling and physiological characterization of *Corynebacterium glutamicum* grown in the presence of L-valine," Applied and Environmental Microbiology, vol. 69, No. 5, May 2003, pp. 2521-2532 [XP002401827].

Lemieux et al., "Application of Reversed-Phase High-Performance Liquid Chromatography to the Separation of Peptides from Phosphorylated Anddephosphorylated Casein Hydrolysates," Science Publishers B.V., Amsterdam, NL, vol. 473, No. 1, 1989, pp. 189-206 [XP 009070046].

Lemieux et al., "High Performance Liquid Chromatography of Casein Hydrolysates Phosphorylated and Dephosphorylated," Jounal of Chromatography, Science Publishers B.V., Amsterdam, NL, vol. 519, No. 2, Nov. 2, 1990, pp. 299-321 [XP 009070060].

Lemieux et al., "Separation of a Casein Hydrolyzate by HPSEC with a New Mobile Phase and Characterization of Peptides by FABMS," Analytica Chimica Acta, Amsterdam, NL, vol. 352, No. 1-3, Oct. 10, 1997, pp. 399-409 [XP 009070061].

Van Der Ven Cornelly et al., "Reversed phase and size exclusion chromatography of milk-protein hydrolysates: Relation between elution from reversed phase column and apparent molecular weight distribution," International Dairy Journal, vol. 11, No. 1-2, 2001, pp. 83-92 [XP002401826].

Aoyama T et al., "Effect of Soy and Milk Whey Protein Isolates and their Hydrolysates on Weight reduction in Genetically Obese Mice" Bioscience Biotechnology Biochemistry, vol. 64, No. 12, Dec. 2000, pp. 2594-2600.

Cordier-Bussat M et al., "Peptones Stimulate Both the Secretion of the Incretin Hormone Glucagon-Like Peptide 1 and the Transcription of the Proglucagon Gene," Diabetes, vol. 47, No. 7, Jul. 1998, pp. 1038-1045.

Cuber J.C. et al., "Luminal CCK-Releasing Factors in the Isolated Vasculary Perfused Rat Duodenojejunum," American Journal of Physiology, vol. 259, No. 2, Part 1, 1990, pp. G191-G197.

Perpetuo, E.A, et al. Biochemical and Pharmacological Aspects of Two Bradykinin-Potentiating Peptides Obtained from Tryptic Hydrolysis of Casein, Journal of Protein Chemistry, vol. 22, Nos. 7/8, Nov. 2003, pp. 601-606.

Marie Claude, R. et al., "Identification of Angiotensin-I-Converting Enzyme Inhibitory Peptides Derived from Sodium Caseinate Hydrolysates Produced by Lactobacillus Hleveticus NCC 2765," Journal of Agricultural and Food Chemistry, vol. 52, No. 23, Nov. 17, 2004, pp. 6923-6931.

International Search Report mailed Feb. 26, 2007 in International Application No. PCT/NL2006/050301.

Office Action mailed Sep. 17, 2009 in U.S. Appl. No. 11/597,722.

Office Action mailed May 12, 2010 in U.S. Appl. No. 11/597,722.

US Office Action mailed Apr. 27, 2010 in U.S. Appl. No. 12/095,346.

Meneilly, G.S. et al., "Effects of 3 Months of Continuous Subcutaneous Administration of Glucagon-Like Peptide 1 in Elderly Patients with Type 2 Diabetes" Diabetes Care, vol. 26: 2835-2841, (2003).

* cited by examiner

PROTEIN HYDROLYSATE ENRICHED IN PEPTIDES INHIBITING DPP-IV AND THEIR USE

The present invention relates to a protein hydrolysate enriched in certain peptides, such isolated peptides, and the use of such protein hydrolysate or isolated peptide for the manufacture of a medicament, food supplement, beverage or food product for prophylaxis and/or treatment of a DPP-IV mediated condition.

BACKGROUND

Dipeptidyl peptidase IV (DPP-IV) is a multifunctional transmembrane glyco-protein that contains N-terminal dipeptidase activity. It is present on most mammalian cells, in a variety of tissues such as liver, kidney, small intestine, salivary gland, blood cells and plasma. Little is however known about the physiological role of DPP-IV.

DPP-IV has been implicated in cellular processes involving immune, inflammatory and endocrine functions. In vitro, DPP-IV has been shown to cleave many hormones and chemokines, such as e.g. glucagon-like peptide 1 (GLP-1).

GLP-1 is an incretin hormone that is released postprandially. GLP-1 has multifaceted actions, including glucose-induced stimulation of insulin biosynthesis and secretion, inhibition of glucagon secretion, regulation of gene expression, trophic effects on β cells, inhibition of food intake, and slowing of gastric emptying. These effects contribute to the normalisation of elevated blood glucose, as well as to the control of satiety and body weight. GLP-1 has been shown to reduce postprandial and fasting glycemia in subjects with type 2 diabetes mellitus and may therefore be a potentially useful new therapeutic agent in the treatment of type 2 diabetes mellitus. Moreover, GLP-1 could be used to increase satiety and also to prevent and treat obesity. See e.g. Conarello, S. L. et al. 2003, *Proc. Nat. Acad. Sci. USA*, vol. 100:6825-6830; Deacon, C. F. et al. 1998, *Diabetes*, vol. 47:764-769; Ahrén, B. et al. 2002, *Diabetes Care*, vol. 25:869-875; Näslund, E. et al. 1998, *Am. J. Clin. Nutr.*, vol. 68:525-530; Meneilly, G. S. et al. 2003, *Diabetes Care*, vol. 26:2835-2841.

However, GLP-1 is rapidly degraded in plasma and therefore has a very short half-life of about 1-2 min. The enzyme mainly responsible for degradation of GLP-1 is DPP-IV. Inhibition of DPP-IV might therefore result in prolongation of the circulating half-life of GLP-1, such that GLP-1 levels increase as to be able to act as a therapeutic agent.

DPP-IV has also been shown to be involved in T cell activation and growth. In the immune system, DPP-IV is expressed primarily on the surface of T cells. It has been shown that the expression of DPP-IV is rapidly increasing upon mitogenic or antigenic stimulation. Moreover, it has been shown that inhibition of DPP-IV can suppress the activation of antigen-induced T cell clones and could thus be useful for therapeutic interventions in immune diseases, in particular in autoimmune diseases, such as e.g. MS, and rheumatoid arthritis. Conversely, DPP-IV inhibitors stimulate the production of the immunoregulatory cytokine TGF-β1. See e.g. Reinhold, D. et al. 2000. Cellular Peptidases in Immune Functions and Diseases 2, Langner and Ansorge ed., Kluwer Academic/Plenum Publishers, 155-160; Steinbrecher, A. et al. 2000, Cellular Peptidases in Immune Functions and Diseases 2, Langner and Ansorge ed., Kluwer Academic/Plenum Publishers, 145-153; and Tanaka S. et al., 1997. *Int. J. Immunopharmac.*, vol. 19:15-24.

Currently, several chemical compounds are used in vitro and in animal models to inhibit DPP-IV activity, such as e.g. valine-pyrrolidide (Deacon, C. F. et al., supra), 1-[[2-[(5-cyanopyridin-2-yl)amino]ethylamino]acetyl]-2-cyano-(S)-pyrrolidine (Ahrén, et al., supra), Lys[Z($NO_2$)]-thiazolidide and Lys[Z($NO_2$)]-pyrrolidide (Reinhold, et al., supra). However, such chemical compounds have the disadvantage that they often have to be administered by injection, and they may result in side effects as chemical drugs often do.

Proteins, in particular milk proteins, are commonly known as precursors of a range of biologically active peptides. The fact that proteins are precursors of biologically active molecules is particularly attractive for the development of functional foods, such as foods that may aid in any of the above DPP-IV mediated conditions. Food protein hydrolysates are well-used food ingredients and are of natural origin, such that no synthetic ingredients are required for obtaining the functional effect, in case the inhibition of DPP-IV as to prevent or treat DPP-IV mediated conditions such as obesity, type 2 diabetes mellitus and immunological disorders.

Thus, it is desired to provide protein hydrolysates that inhibit DPP-IV activity such that they may aid in prevention and treatment of the above-identified DPP-IV mediated conditions. It was found that protein hydrolysates, such as e.g. milk protein hydrolysates could be used for inhibiting DPP-IV. However, the factors within such hydrolysate that are responsible for such inhibition are as yet unknown. Hydrolysed protein samples are highly complex and can contain up to hundreds of different molecules, which makes it difficult to identify the bioactive compounds in such a sample.

DESCRIPTION OF THE INVENTION

Figure 1:
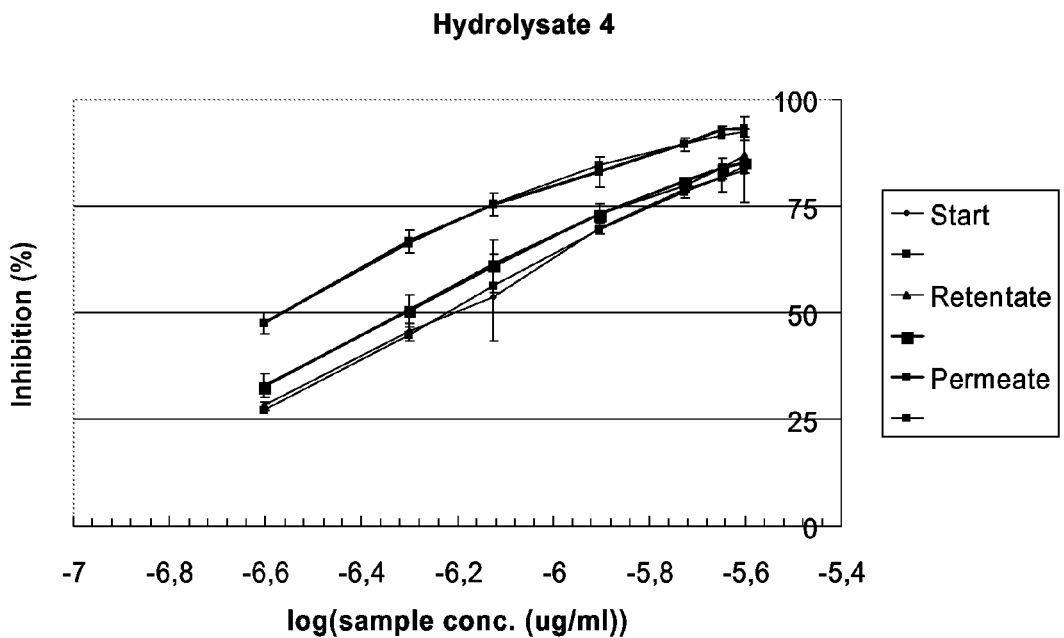
FIG. 1 shows the DPP-IV inhibiting effect of the starting material, the dried centrifugation pellet, the dried UF retentate and the dried UF permeate of a hydrolysate 4 obtained by bromelain treatment of sodium caseinate.

The present inventors have now identified bioactive peptides from protein hydrolysates that inhibit DPP-IV activity. Such bioactive peptides or a protein hydrolysate enriched in such bioactive peptides can advantageously be used for the natural prevention and treatment of DPP-IV mediated conditions such as for example obesity, type 2 diabetes mellitus and immunological disorders. About 40 protein hydrolysates were subjected to on-line liquid chromatography (LC)-biochemical detection (BCD)-mass spectrometry (MS), a method that allowed for separation of crude extract by HPLC, after which the presence of bioactive compounds was detected by means of an on-line biochemical assay. This method for on-line fractionation and characterisation has extensively been described by Van Elswijk et al. (*J Chromatography A* (2003) 1020:45-58).

Thus, in a first aspect the present invention relates to a protein hydrolysate having DPP-IV inhibiting activity, the hydrolysate being enriched in peptides having a length of 2-8 amino acids comprising at least one proline residue. It was found that such peptides were capable of inhibiting DPP-IV activity in vitro, and could thus be used for prophylaxis and/or treatment of a DPP-IV mediated condition, such as obesity, type 2 diabetes mellitus or an immunological disorder.

It is well documented that DPP-IV displays a preference for substrate having a proline (P) (and to a lesser extent Ala; A) as the second N-terminal residue (penultimate N-terminal residue), with a preference for lysine (K) and arginine (R) as the ultimate N-terminal residue (Davy et al. *Plant Physiol.* (2000) 122:425-432).

From about 40 protein hydrolysates, the present inventors identified about 21 peptide sequences that were capable of inhibiting DPP-IV activity. These peptides have a length varying from 3-7 amino acids and are generally characterised by a hydrophobic character and in particular the presence of a proline (P) residue within the peptide sequence. The inhibiting peptides comprise a proline residue as the first, second, third or fourth N-terminal residue, but mostly as second N-terminal residue. The proline is also found as C-terminal residue or penultimate C-terminal residue. The proline residue is mostly flanked by leucine, valine, or phenylalanine (F), but may also to a lesser extent be flanked by glutamine (Q), alanine, histidine (H), isoleucine (I), glycine (G), methionine (M), and tyrosine (Y). Out of 21 peptide sequences, only one inhibiting sequence was identified wherein the proline residue was flanked by a charged residue, which flanking charged residue is histidine. Similarly, out of the polar amino acids serine, threonine, asparagine and glutamine, only glutamine was identified as flanking residue in the peptides found to inhibit DPP-IV. Most potent DPP-IV inhibitory activity was found for peptides wherein the proline residue is located on the second N-terminal position, and when this proline residue is flanked on either side by valine, isoleucine and/or leucine most preferably flanked by leucine on one or both sides.

As herein used, "protein hydrolysate" refers to a mixture of peptides derived from hydrolysis of one or more proteins with a minimal degree of hydrolysis, i.e. the percentage of hydrolysed peptide bonds of the total amount of peptide bonds, of 5%, preferably of 10%, more preferably of 20%, most preferably of 30%. The preferred degree of hydrolysis is between 5 and 70%, most preferred between 10 and 50%, most preferably 20-40%. It is preferred that the hydrolysate contains between 20 and 100 wt. %, more preferred between 25 and 75%, most preferred between 30 and 60 wt. % of peptides of 2-8 amino acids. Especially preferred are hydrolysates containing between 20 and 80 wt. %, most preferred between 30 and 60 wt. % of peptides of 3-7 amino acids. Preferably, the weight percentage of peptides having a molecular weight over 500 Da is less than 75%, preferably less than 70%, and the weight percentage of peptides having a molecular weight over 1000 Da is less than 50%, preferably less than 35%.

The protein can be derived from one protein source or may be derived from more protein sources. Examples of such protein sources are microorganisms (yeast, bacteria, fungi), plants (e.g. soy, pea, cotton, corn, wheat), animals, and from animal derived protein sources such as milk, blood, meat, egg and gelatine. Thus, the one or more proteins may be e.g. protein from microorganisms, vegetable protein, animal protein, such as protein derived from meat scraps, fish, crustaceans or molluscs, milk protein and egg protein.

Said hydrolysis of proteins can be performed by any means known in the art. Examples thereof include methods for chemical hydrolysis or enzymatic hydrolysis. Non-limiting examples of methods for chemical hydrolysis are well known in the art and comprise e.g. hydrolysis using cyanogen bromide, acid hydrolysis, e.g. using hydrochloric acid or hydrolysis by means of fermentation of the one or more protein sources comprising the one or more proteins. Non-limiting examples of methods for enzymatic hydrolysis are also well known in the art and comprise hydrolysis using purified enzyme preparations or crude enzyme preparations. Enzyme preparations to be used may comprise endo- or exo-peptidases, proteases, or mixtures thereof, and examples thereof include trypsin, chymotrypsins A, B and C, pepsin, rennin, microbial alkaline proteases, papain, ficin, bromelain, cathepsin B, collagenase, microbial neutral proteases, carboxypeptidases A, B and C, carnosinase, anserinase, V8 protease from *Staphylococcus aureus* and many more which are well known to a person skilled in the art. Also combinations of these proteases may be used. Also commercially available enzyme preparations such as e.g. Alkalase, Chymotrypsine 800s, Neutrase, Flavourzyme (all available from Novo Nordisk, Denmark), Protex 6.0L, Peptidase FP (both available from Genencor, USA), Corolase L10 (Rohm, Germany), Pepsin (Merck, Germany), papain, pancreatin, proleather N and Protease N (Amano, Japan), or combinations thereof may be used. Enzymes prepared by means of recombinant DNA technology may also be used.

The protein hydrolysate is preferably obtained by cleavage of the protein using an enzyme that results in peptides with a N-terminal penultimate proline residue. Such enzyme can e.g. be one or more cysteine endoproteases, such as the Cys endoproteases EP-A and EP-B, but may also be any of the other suitably enzymes as discussed above.

The protein hydrolysates having DPP-IV inhibiting activity are considered "enriched in peptides having a length of 2-8 amino acids comprising at least one proline residue" if the DPP-IV inhibiting activity measured as set forth below is increased with respect to the starting protein hydrolysate, and/or the presence of such peptides can be demonstrated by means of common protein or peptide fractionation and analysis techniques, such as for example mass spectrometry as set forth in Van Elswijk et al. (supra), but also other techniques such as HPLC or other fractionation techniques in combination with e.g. sequential Edmann degradation or specific affinity assays targeted towards a certain peptide, such as an ELISA. The protein hydrolysates, preferably milk protein hydrolysates, more preferably casein protein hydrolysates, may be fractionated by means of extraction, precipitation, filtration, ultrafiltration, nanofiltration, microfiltration or conventional column chromatography (preferably ion exchange or affinity chromatography), or any combination of the above techniques, as to (further) isolate the DPP-IV inhibitory activity. As such, a fraction comprising a mixture of peptides or even single peptides may be identified that have an increased inhibitory effect on DPP-IV compared with the starting protein hydrolysates. Such mixture of peptides or single peptides are also encompassed in the present invention. It is further envisioned that such peptides may be prepared by means of recombinant DNA technology, such as expression of the DNA encoding therefore in a suitable host, or by chemical synthesis.

The protein hydrolysate may be any protein hydrolysate, in particular a food protein hydrolysate, as such hydrolysate is considered food grade and relatively easy to obtain.

As used herein, a hydrolysate displays "DPP-IV inhibiting activity" when in the DPP-IV inhibition assay of example 1 an $IC_{50}$ (i.e. the concentration of inhibitor (in particular protein hydrolysate) that inhibits 50% of the DPP-IV activity) is displayed of at most 1000 µg/ml, preferably 800 µg/ml, more preferably 600 µg/ml, yet more preferably 400 µg/ml, and most preferably at most 300 µg/ml.

In a preferred embodiment of the present invention, the protein hydrolysate is a milk protein hydrolysate, as proline is abundant in milk protein hydrolysates and several of the peptide sequences identified in the present invention are found in milk protein, and are thus readily obtainable. It has been found that milk protein hydrolysate provides the envisaged DPP-IV inhibiting activity. The milk may originate from any mammal, especially from cattle, sheep or goat, preferably from cattle (bovine milk).

In a preferred embodiment according to the present invention, the protein hydrolysate is a casein hydrolysate. It was found that many of the peptide sequences identified in the present invention are found in one or more of the casein sequences and are therefore readily obtainable from a hydrolysate prepared from casein. In another embodiment, the protein hydrolysate is a whey protein hydrolysate, e.g. from β-lactoglobulin.

In a further preferred embodiment of the present invention, the peptides have a length of 3-7 amino acids. The most potent DPP-IV inhibitors were found to have such length.

Preferred peptides contain one of the tripeptide sequences ZPX and XPZ, wherein Z is leucine (L), isoleucine (I), valine (V) or phenylalanine (F), and X is Z or glutamine (Q), alanine (A), histidine (H), glycine (G), methionine (M) or tyrosine (Y). Examples thereof include IPI, LPL, VPF, FPI, LPA, IPY, LPQ, HPI, GPF, MPL, etc. These tripeptide sequences may be part of peptides of 3-8 amino acids, wherein the other amino acids are preferably those as found in natural proteins, such as wheat, soy and milk proteins. Examples of peptides derived from milk proteins are the following: KHPIKHQ (SEQ ID NO: 1), GLPQEVL (SEQ ID NO: 2), VAPFPEV (SEQ ID NO: 3), KVPQLEI (SEQ ID NO: 4), YVPLGTQ (SEQ ID NO: 5), MPLW (SEQ ID NO: 6), QGPIVLN (SEQ ID NO: 7), AVPITPT (SEQ ID NO: 8), VIPYVRYL (SEQ ID NO: 9), YPFPGPIP (SEQ ID NO: 10), PGPIPNS (SEQ ID NO: 11), S LPQNIPPL (SEQ ID NO: 12), IPPLTQT (SEQ ID NO: 13), ILPLTQT (SEQ ID NO: 14), VVPPFLQ (SEQ ID NO: 15), E MPFPKY (SEQ ID NO: 16), KYPVEPF (SEQ ID NO: 17), HLPLPLL (SEQ ID NO: 18), KVLPVPQK (SEQ ID NO: 19), AVPYPQR (SEQ ID NO: 20), MPIQAFL (SEQ ID NO: 21), GPFPIIV (SEQ ID NO: 22), TLPFLGA (SEQ ID NO: 23), YIPIQYV (SEQ ID NO: 24), FLPYPYY (SEQ ID NO: 25), SAPLRVY (SEQ ID NO: 26), KIPAVFK (SEQ ID NO: 27) and ALPMHIR (SEQ ID NO: 28), wherein preferred peptides are those having at least a tripeptide sequence as underlined, and further having from zero up to four or five of the surrounding amino acids, with a further preference for peptides wherein the proline residue (P) is the second residue from the N-terminus. These peptides can be used as such or in any mixture, in particular as a part of a hydrolysate.

In a more preferred embodiment, the peptides that are enriched in the protein hydrolysate according to the present invention are chosen from LPL, IPI, PFP, LPLP (SEQ ID NO: 29), HPIK (SEQ ID NO: 30), LPVP (SEQ ID NO: 31), MPLW (SEQ ID NO: 6), GPFP (SEQ ID NO: 32), PLLQ (SEQ ID NO: 33), KVLP (SEQ ID NO: 34), APFPE (SEQ ID NO: 35), LPQYL (SEQ ID NO: 36), LPVPQ (SEQ ID NO: 37), VPYPQ (SEQ ID NO: 38), APFPEVF (SEQ ID NO: 39), GPFPIIV (SEQ ID NO: 22), EMPFPK (SEQ ID NO: 40), PQSVLS (SEQ ID NO: 41), YVPEPF (SEQ ID NO: 42), VPLGTQ (SEQ ID NO: 43), and LPVPQK (SEQ ID NO: 44), and truncated peptides derived from these peptides having at least 3 amino acids including one or two proline residues. By means of online LC-BCD-MS it was found that these particular peptides are potent inhibitors of DPP-IV and can thus be advantageously employed in the prophylaxis and/or treatment of DPP-IV mediated conditions such as obesity, type 2 diabetes mellitus and immunological disorders.

It is most preferred that the peptides that are enriched in the protein hydrolysate according to the present invention are chosen from the group, consisting of VPYPQ (SEQ ID NO: 38), VPLGTQ (SEQ ID NO: 43), LPVPQK (SEQ ID NO: 44), KVLP (SEQ ID NO: 34), LPL and IPI. These peptides were identified as most potent DPP-IV inhibitors, and are therefore of particular interest.

In a further aspect, the present invention relates to an isolated peptide derivable from a protein hydrolysate, said peptide having DPP-IV inhibiting activity and having a length of 2-8 amino acids comprising at least one proline residue, said peptide being chosen from the group, consisting of LPL, IPI, PFP, LPLP (SEQ ID NO: 29), HPIK (SEQ ID NO: 30), LPVP (SEQ ID NO: 31), MPLW (SEQ ID NO: 6), GPFP (SEQ ID NO: 32), PLLQ (SEQ ID NO: 33), KVLP (SEQ ID NO: 34), APFPE (SEQ ID NO: 35), LPQYL (SEQ ID NO: 36), LPVPQ (SEQ ID NO: 37), VPYPQ (SEQ ID NO: 38), APFPEVF (SEQ ID NO: 39), GPFPIIV (SEQ ID NO: 22), EMPFPK (SEQ ID NO: 40), PQSVLS (SEQ ID NO: 41), YVPEPF (SEQ ID NO: 42), VPLGTQ (SEQ ID NO: 43), and LPVPQK (SEQ ID NO: 44), or a mixture of two or more thereof. It was found that these peptides in particular were very potent DPP-IV inhibitory compounds (see e.g. example 1). It is to be further noted that additional peptides, namely LF, LL, II, LC and VTKCCTE (SEQ ID NO: 45) were found to be DPP-IV inhibiting compounds. The DPP-IV inhibition assay was performed in vitro and is therefore indicative of DPP-IV inhibiting activity; one skilled in the art is however aware of the fact that the compounds showing only moderate DPP-IV inhibiting activity may work substantially improved in vivo. It is preferred that the peptide has a length of 3-7 amino acids, as is discussed above.

One skilled in the art is aware of suitable methods for obtaining the peptides according to the present invention, such as e.g. by fractionation of a suitable protein hydrolysate, such as for example a casein hydrolysate, or synthesis by means of recombinant DNA technology or chemical synthesis. These are standard methods for obtaining such peptides.

In a preferred embodiment, the isolated peptide according to the present invention is chosen from the group, consisting of VPYPQ ISEQ ID NO: 38), VPLGTQ (SEQ ID NO: 43), LPVPQK (SEQ ID NO: 44), KVLP (SEQ ID NO: 34), LPL and IPI, or the mixture according to the present invention is chosen from two or more of said group, for the same reasons as discussed above.

In a third aspect, the present invention relates to the use of a protein hydrolysate according to the present invention or an isolated peptide or mixture according to the present invention for the manufacture of a medicament, food supplement, beverage or food product for prophylaxis and/or treatment of a DPP-IV mediated condition.

The term "prophylaxis" as herein used refers to preventing the emergence of a DPP-IV mediated condition in case no symptoms are as yet observed. As such, the one or more protein hydrolysates may be employed to prevent deleterious DPP-IV mediated conditions from occurring, and may therefore be used to improve or stabilise health of any subject, in particular of a subject in need thereof.

As herein used, "a DPP-IV mediated condition" refers to any deleterious condition that arises (at least partially) or deteriorates due to the action of DPP-IV, such that DPP-IV plays an important role in the pathogenesis. Non-limiting examples of a DPP-IV mediated condition are disorders such as obesity, type 2 diabetes mellitus, and immunological disorders, such as autoimmune diseases, e.g. multiple sclerosis, rheumatoid arthritis, and Graves' disease. Other autoimmune diseases envisioned to benefit from inhibition of DPP-IV are type 1 diabetes mellitus, autoimmune haemolytic anaemia, Hashimoto's thyroiditis, myasthenia gravis, Goodpasture's syndrome, systemic lupus erythematosus, primary biliary cirrhosis, Sjögren's syndrome, chronic active hepatitis, mixed connective tissue disease, scleroderma, and chronic idiopathic thrombocytopenic purpura.

In an embodiment of the present invention, the DPP-IV mediated condition is chosen from the group, consisting of obesity, type 2 diabetes mellitus, and an immuno-logical disorder. The involvement of DPP-IV in the pathogenesis of these disorders is well described in the literature and these disorders are therefore the major target of the hydrolysate or peptide according to the present invention.

In one embodiment, the protein hydrolysate or isolated peptide according to the present invention is used for the manufacture of a medicament, food supplement, beverage or food product for increasing satiety in a subject. As GLP-1 slows gastric emptying and inhibits food intake, a longer circulation half-life of GLP-1 as a result of inhibition of the degradation enzyme DPP-IV will increase satiety in a subject, such that said subject will feel less hungry and have a reduced food intake. In particularly subjects being overweight, such as e.g. obese subjects or subjects being only slightly overweight, will benefit from inhibition of DPP-IV by administration of the one or more protein hydrolysates according to the present invention. The medicament, food supplement, beverage or food product can however also be employed as to retain a certain weight as to not get overweight, and may therefore be used to stabilise and/or improve the body weight as for cosmetic purposes, i.e. for stabilising and/or improving appearance.

Therefore, in a further embodiment the protein hydrolysate or isolated peptide according to the present invention is used for the manufacture of a medicament, food supplement, beverage or food product for prophylaxis and/or treatment of obesity. For reasons as set out above, administration of the one or more protein hydrolysates according to the present invention is likely to be advantageous in the prophylaxis and/or treatment of obesity.

In another embodiment the protein hydrolysate or isolated peptide according to the present invention is used for the manufacture of a medicament, food supplement, beverage or food product for lowering of blood glucose levels. It has been found that blood glucose levels are reduced by ingestion of the hydrolysates, resulting in improved glucose management, which is particularly advantageous in diabetic subjects.

In a further embodiment the protein hydrolysate or isolated peptide according to the present invention is used for the manufacture of a medicament, food supplement, beverage or food product for increasing the pancreatic β-cell mass. It has been found that pancreatic β-cell mass increases by ingestion of the hydrolysate or peptides results in an improved insulin response and hence an improved glucose management, which is particularly advantageous in diabetic subjects.

In yet a further embodiment, the protein hydrolysate or isolated peptide according to the present invention is used for the manufacture of a medicament, food supplement, beverage or food product for prophylaxis and/or treatment of type 2 diabetes mellitus. Type 2 diabetes mellitus is characterised by resistance to insulin, such that the body does not respond to insulin appropriately, resulting in hyperglycaemia. It is often accompanied by obesity. As GLP-1 contributes to normalisation of blood glucose levels as well as to the control of satiety and obesity (body weight), increase of GLP-1 levels by increasing the circulation half-life thereof as a result of inhibition of DPP-IV, it is expected that inhibition of DPP-IV by administration of the one or more protein hydrolysates according to the present invention contributes to prophylaxis and/or treatment of type 2 diabetes mellitus.

In yet another embodiment, the protein hydrolysate or isolated peptide according to the present invention is used for the manufacture of a medicament, food supplement, beverage or food product for prophylaxis and/or treatment of an immunological disorder. As discussed above, DPP-IV is thought to play an important role in the pathogenesis of certain immunological disorders. Inhibition of DPP-IV is considered to have a beneficial effect on such immunological disorders, such that the administration of the one or more protein hydrolysates according to the present invention, inhibiting DPP-IV activity, may result in the prophylaxis and/or treatment of such immunological disorder.

It is preferred that such immunological disorder is an autoimmune disease, as suppression of such diseases by inhibition of DPP-IV has been well established (supra). Preferably, said autoimmune disease is chosen from rheumatoid arthritis, multiple sclerosis and Graves' disease, for the same reason as set forth above.

For use in a medicament or food supplement, said preparation can be combined with any suitable carrier, diluent, adjuvant, excipient, etc. in order to obtain the medicament in the desired administration form. Advantageously, said medicament or food supplement is administered orally. The term "food supplement" is known in the art as any food component which provided specific nutritional or medicinal components and does not provide the full energy value required (i.e. generally less than 2000 or 2500 kcal/day) and includes food supplements in the form of a powder or medicament, as well as health products, such as health drinks. An ingredient that can be added to food before consumption or a preparation that can be consumed as such is also encompassed.

For the intended use, the protein hydrolysate or isolated peptide according to the present invention may be administered alone or in admixture with a pharmaceutically acceptable carrier, in suitable pharmaceutical formulations which are a further object of the invention.

Examples of said formulations, which may be prepared using well known methods and excipients, such as those described in "Remington's Pharmaceutical Sciences Handbook", Mack Pub. Co., N.Y. U.S.A., are tablets, capsules, syrups, and the like for oral administration, whereas for the parental administration suitable forms are sterile solutions or suspensions in acceptable liquids, implants, etc.

The posology will depend on several factors such as type and seriousness of the pathological conditions to be treated, patient's weight and sex, etc. and will be easily determined by the skilled practitioner. Preferably, the hydrolysates of the invention are administered at a level of between 2 mg and 10 g, depending i.a. on the concentration of active peptides. Preferred dosage levels of the hydrolysates are between 10 mg and 5 g, more preferably between 50 mg and 1 g per day. As to active fractions, in particular the fraction of peptides having 2-8 amino acids, the preferred level of administration is between 1 mg and 1 g of peptide mixture per individual per day, more preferred dosage levels for this fraction is between 10 and 500 mg/day.

For use in a beverage or food product, the protein hydrolysate or isolated peptide or mixture thereof according to the present invention can be combined with any common food ingredient. The term "beverage" is meant to include cordials and syrups, as well as formulations of a dry powder to be dissolved in water or another liquid component for the preparation of instant drinks.

The molecular weight of the peptides within the hydrolysate according to the present invention may vary depending on the molecular weight of the one or more protein sources. In case of a high degree of hydrolysis, the peptides will generally be of smaller molecular weight than in case of a lower degree of hydrolysis.

It is preferred that the one or more protein hydrolysates are obtained by enzymatic hydrolysis as discussed above, as enzymatic hydrolysis provides a suitable degree of hydrolysis and is conveniently performed. Moreover, the enzymes employed for enzymatic hydrolysis can be easily separated from the protein hydrolysate by means of simple column chromatography, such as e.g. gel filtration chromatography, or be inactivated by means of heat, acid, base, or the addition of inhibitors.

Preferably, the protein hydrolysate or the isolated peptide according to the present invention is administered in an amount of 0.0001-0.1 g/kg body weight, depending type and seriousness of the pathological condition to be treated, weight and sex of the subject, etc. Such factors will easily be determined and taken into account by the skilled practitioner. Using such range, sufficient inhibition of DPP-IV will be achieved as to effect the desired inhibition of DPP-IV required for prophylaxis and/or treatment of the herein disclosed disorders and diseases.

The present invention is also directed to a method for prophylaxis and/or treatment of any DPP-IV mediated condition as discussed above, said method comprising administering an effective amount of the protein hydrolysate or the isolated peptide according to the present invention to a subject in need thereof.

The following examples are employed to further illustrate the present invention, but are in no way meant to limit the scope thereof.

EXAMPLES

Example 1

In Vitro Measurement of DPP-IV Activity

DPP-IV activity can be determined by measuring the increase in absorption at 385 nm using Gly-Pro-p-nitroanilide (Sigma G-0513) as DPP-IV substrate. A decrease in DPP-IV activity is a measure for the inhibition.

13.152 mg Gly-Pro-p-nitroanilide (substrate; Sigma G-0513) was dissolved in 1 ml Tris buffer, pH 8.0. DPP-IV (Sigma D-7052) was diluted with Tris buffer, pH 8.0 to 1.1 Unit/ml. The substrate was diluted 50-fold with Tris buffer, pH 8.0. The samples were prepared by diluting a protein hydrolysate to a 1 wt. % protein solution in Tris buffer, pH 8.0. The samples were then serially diluted to obtain a range of sample concentrations. 50 µl of the different serially diluted samples and 50 µl of the diluted substrate were then pipetted in wells of a microtiter plate with 96 wells. Subsequently, 100 µl of the diluted enzyme was pipetted in each well of a plate with 96 wells. Then the increase in absorption at 385 nm was determined and DPP-IV activities at different concentrations of a variety of protein hydrolysates were determined, from which the $IC_{50}$ (i.e. the concentration of inhibitor (particular protein hydrolysate) that inhibits 50% of the DPP-IV activity) could be derived. All hydrolysates had a degree of hydrolysis (DH) of more than 5%. As a control, two unhydrolysed proteins (Sodium caseinate from DMV International, NL, and Bipro from Davisco Foods, USA) with a degree of hydrolysis (DH) of 0% were tested. The degree of hydrolysis was determined using the o-phtaldialdehyde method, which is well known in the art. Thus, it was determined that many protein hydrolysates, in particular casein hydrolysates, had an $IC_{50}$ in the range of 290-1000 µg/ml, but that unhydrolysed protein did not inhibit the enzyme.

Example 2

Preparation of Protein Hydrolysates Containing DPP-IV-Inhibiting Peptides

Hydrolysate 1

1000 grams of casein (DMV international, NL) was dissolved in 7.2 liters of water. The pH and temperature were adjusted to 8.8 and 55° C., respectively, after which the volume was increased to exactly 8 liters. 40 grams of Alkalase (Novo Nordisk, DK), 4 gram of Protease N (Amano, Japan) and 4 grams of Flavourzyme (Novo Nordisk) were then added to the mixture. After incubation for 18 hours the reaction was stopped by heat inactivation at 90° C. for 10 minutes. After cooling to 50° C. the mixture was passed over a filter membrane having a 3 kDa cut-off, and the permeate was dried.

Hydrolysate 2

1400 grams of casein (DMV international, NL) was dissolved in 7.2 liters of water. The pH and temperature were adjusted to 8.3 and 50° C., respectively, after which the volume was increased to exactly 8 liters. 1.5 grams of Trypsin PTN 6.0 (Novo Nordisk, DK) were added as well as 200 ml of ethanol. The mixture was then incubated for 2 hours under constant stirring. 9 grams of Corolase LAP F (Röhm, DE) were added as well as 100 ml ethanol. After further incubation for 21 hours the reaction was stopped by heat inactivation at 90° C. for 10 minutes. The mixture was subsequently cooled to 50° C. and dried.

Hydrolysate 3

1000 grams of a whey protein concentrate (WPC80; Arla, DK) was dissolved in 7.2 liters of water. The pH and temperature were adjusted to 8.3 and 60° C., respectively, after which the volume was increased to exactly 8.0 liters. 12 grams of Protease N (Amano, Japan) were added as well as 250 ml of ethanol. The mixture was incubated under constant stirring for 18 hours. The reaction was stopped by applying heat for 10 minutes at 90° C. The resulting mixture was cooled to 50° C. and passed over a 3 kDa filter and dried.

Analysis of Hydrolysate 2

The dried hydrolysate 2 was redissolved in water and subject to nanofiltration over a 3 kDa filter membrane. The retentate and permeate were tested for DPP-IV inhibition efficacy and mass balance (retentate & permeate versus total hydrolysate). DPP-IV inhibition was performed as described above in example 1 while for the mass balance the o-phtaldialdehyde method was used. Briefly, this method is based on the modification of primary amine groups, as those present in proteins and peptides, with ortho-phtaldialdehyde. To this end the sample was dissolved in 0.1 M borax, 1% (w/v) sodium dodecylsulfate, pH 9.3. After mixing, the ortho-phtaldialdehyde reagent is added and then incubated for 10 minutes at room temperature. The absorbency was measured at 340 nm. The mass balance was determined by relating the absorbency of the retentate and permeate to the total amount of protein in the hydrolysate. Table 1 shows a two-fold increase in DPP-IV-inhibition activity of the permeate compared to the starting hydrolysate.

TABLE 1

DPP-IV inhibitory efficacy of hydrolysate 2.

| | DPP-IV inhibition (% inhibition per mg dry matter) |
|---|---|
| Total hydrolysate | 75.3 |
| Retentate | 94.2 |
| Permeate | 157.7 |

Example 3

Further Identification of Bioactive Compounds in Protein Hydrolysates

A variety of protein hydrolysates prepared according to example 2 were further investigated for DPP-IV inhibiting activity. Hydrolysed protein samples were analysed for DPP-IV inhibitory activity in a high-resolution screening (HRS) instrument, as discussed in Van Elswijk et al. (supra).

DPP-IV inhibition was monitored via the substrate conversion based bioassay format as disclosed in example 1. In addition to the DPP-IV inhibitory activity data, chemical information was obtained in real-time by allowing part of the HPLC effluent to be directed towards a mass spectrometer. This way, both activity information as well as chemical characteristics of the biochemically active compounds were obtained during a single chromatographic run. The assay conditions applied ensured maximum enzyme activity by applying substrate saturation. The compounds having DPP-IV inhibitory activity are identified in table 2.

TABLE 2

PEPTIDE SEQUENCES OF DPP-IV INHIBITORS

| MASS BIOACTIVE COMPOUND [Da] | PEPTIDE SEQUENCE | SEQ ID NO: | RELATIVE POTENCY [%] |
|---|---|---|---|
| 806.4218 | APFPEVF | 39 | 6 |
| 494.2975 | HPIK | 30 | 6 |
| 560.2591 | APFPE | 35 | 9 |
| 742.4263 | GPFPIIV | 22 | 9 |
| 439.2995 | LPLP | 29 | 11 |
| 748.3701 | EMPFPK | 40 | 12 |
| 425.2841 | LPVP | 31 | 15 |
| 360.2020 | PFP | | 20 |
| 630.3310 | PQSVLS | 41 | 20 |
| 751.3700 | YVPEPF | 42 | 20 |
| 546.2790 | MPLW | 6 | 23 |
| 633.3681 | LPQYL | 36 | 26 |
| 553.3435 | LPVPQ | 37 | 28 |
| 417.2326 | GPFP | 32 | 34 |
| 470.2989 | PLLQ | 33 | 37 |
| 603.3213 | VPYPQ | 38 | 51 |
| 614.3680 | VPLGTQ | 43 | 55 |
| 681.4252 | LPVPQK | 44 | 63 |
| 456.3379 | KVLP | 34 | 98 |
| 342.2429 | LPL | | 100 |
| 342.2429 | IPI | | 100 |

In table 2, the relative potency is the signal displayed by a compound in the DPP-IV inhibition assay of example 1 in comparison to the highest signal obtained in this test (for LPL and IPI). Based on the estimated amounts of the corresponding peptides in the hydrolysates and the IC$_{50}$ of those hydrolysates, it is estimated that 100% potency corresponds with an IC$_{50}$ of about 5 µM, which implies that a relative potency of 6% corresponds with an IC$_{50}$ of about 120 µM.

Example 4

Preparation and Activity of Protein Hydrolysate Containing and Enriched in DPP-IV Inhibiting Activity Hydrolysates 4, 5 and 6

Figure 2:
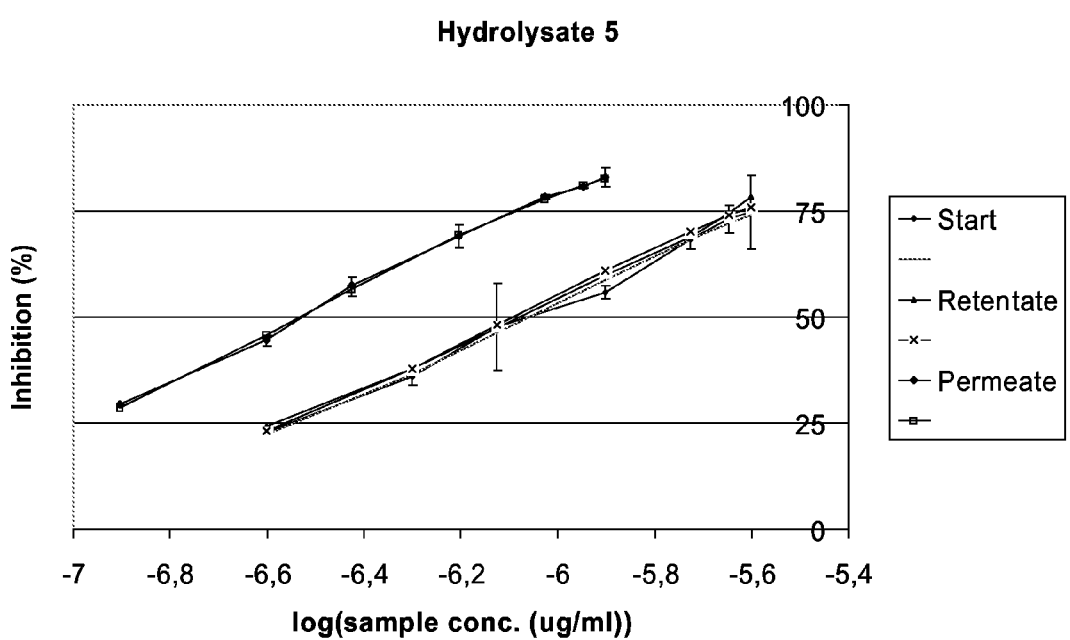
FIG. 2 shows the DPP-IV inhibiting effect of the starting material, the dried centrifugation pellet, the dried UF retentate and the dried UF permeate of a hydrolysate 5 obtained by Scintillase CS150L treatment of sodium caseinate.
Figure 3:
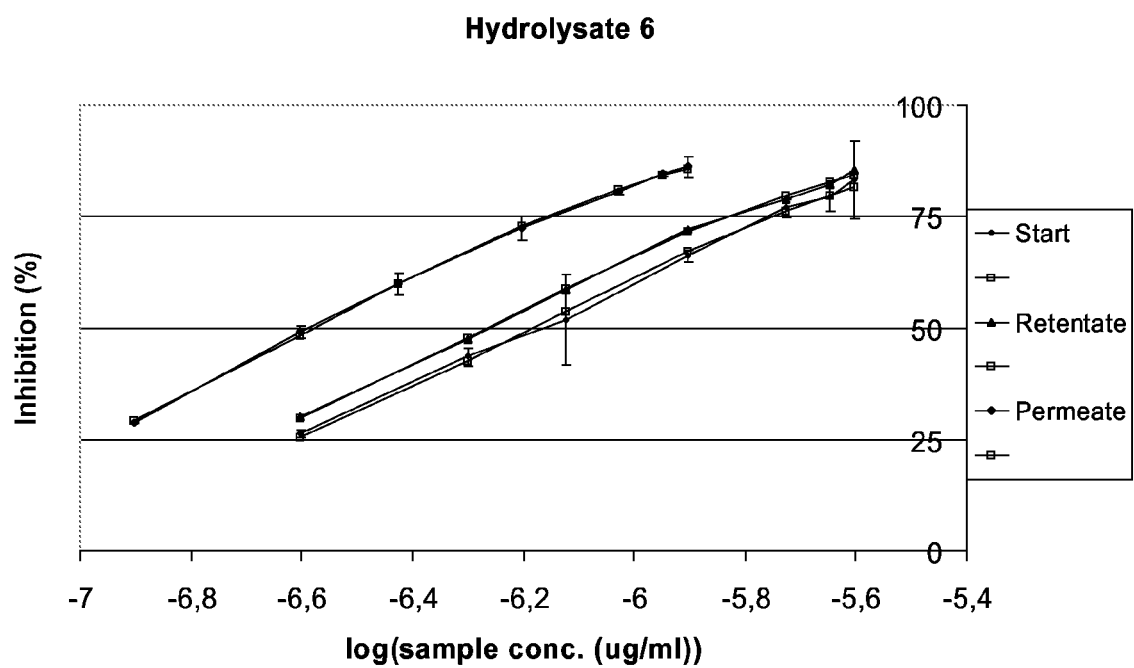
FIG. 3 shows the DPP-IV inhibiting effect of the starting material, the dried centrifugation pellet, the dried UF retentate and the dried UF permeate of a hydrolysate 6 obtained by papain treatment of sodium caseinate.

100 grams of sodium caseinate was dissolved in 1800 g water with stirring. The pH was adjusted to pH 7. Water was then added to a final volume of 2000 ml. 1 gram of the protease as identified in table 3 (bromelain, Scintillase CS150L (Genencor), papain) dissolved in water was added and the mixture was incubated at 50° C. internal temperature for 24 hours. The enzymatic reaction was then stopped by heating at 95° C. for 5 minutes and the mixture was then freeze-dried. The freeze-dried product was redissolved in water and centrifuged at 3000 rpm. The supernatant was diafiltrated over an UF filter with a cut-off value of 1 kDa. The DPP-IV inhibiting effect of the starting material, the dried centrifugation pellet, the dried UF retentate and the dried UF permeate was determined (table 3, FIGS. 1, 2, 3).

TABLE 3

IC50 values (microgram/ml) and enrichment of dried hydrolysate fractions

| protease | Hydrolysate 4 bromelain | Hydrolysate 5 Scintillase CS150L | Hydrolysate 6 papain |
|---|---|---|---|
| Starting material | 600 | 875 | 655 |
| Pellet | N.D. | 2020 | 1402 |
| Retentate | 492 | 811 | 544 |
| Permeate | 290 | 293 | 267 |
| Enrichment in permeate | 2.07 | 2.99 | 2.46 |

(N.D. = not detectable)

Example 5

Preparation of Tablets Containing DPP-IV-Inhibiting Hydrolysate

| Tablet weight 850 mg. | |
|---|---|
| | Per 100 g |
| Hydrolysate 2 according to example 2 | 88.24 g |
| Microcrystalline cellulose[1] | 10.59 g |
| Silicon Dioxide[2] | 0.47 g |
| Magnesium Stearate | 0.35 g |
| Stearic Acid | 0.35 g |

[1]Avicel PH-102-FMC
[2]CAB-O-SIL M-5

The powders were premixed whilst the Mg stearate was withheld for the last minutes of mixing. The tablets were prepared by direct compression (compression pressure 20 kN, hardness: 160 N).

Example 6

Preparation of a Chocolate Caramel Bar Containing DPP-IV-Inhibiting Hydrolysate

|  | Per 100 g | per Serving (40 g) |
|---|---|---|
| Hydrolysate 2 of example 2 | 8.30 g | 3.32 g |
| Maltitol Syrup[1] | 66.01 g | 26.41 g |
| Calcium Caseinate | 10.65 g | 4.26 g |
| Chocolate Liquor | 8.52 g | 3.41 g |
| Sodium Caseinate, granular | 4.26 g | 1.70 g |
| Cocoa Butter | 2.13 g | 0.85 g |
| Butter, Unsalted | 0.11 g | 0.04 g |
| Lecithin | 0.01 g | 0.0043 g |
| Vanilla Flavour | 0.01 g | 0.0043 g |

[1]Lycasin 85% solution

Example 7

Preparation of a Heat-Treated Yoghurt Drink Containing DPP-IV-Inhibiting Hydrolysate

|  | Per 100 g |
|---|---|
| Hydrolysate 2 of example 2 | 0.86 g |
| Skimmed milk | 55 g |
| Sugar | 6 g |
| Maltitol[1] | 3 g |
| Lactic acid | 0.002 g |
| Pectin[2] | 0.3 g |
| Flavour | 0.055 g |
| Water | 34.6 g |
| Inoculum[3] | 0.2 g |

[1]C*maltidex 16385 Cerestar
[2]Genu Pectine YM-115-H CP Kelco
[3]YC-X11 Christian Hansen Milk was mixed with water. The hydrolysate 2 according to example 3, sugar and maltitol were added and dissolved with continuous stirring followed by pasteurisation (90° C., 5 min). After cooling to the fermentation temperature (42° C.), the inoculum was added. Fermentation was proceeded until the pH reached 4.3. The pH was lowered to 3.8-4.0 using lactic acid. The pectin was added under vigorous stirring. The mixture was heated to 70° C., homogenised at 120/20 bar and flavour was added. After filling, the product was pasteurised (80° C./3 min).

Example 8

Preparation of a Drink Containing DPP-IV-Inhibiting Hydrolysate

|  | Per 100 g | per Serving (250 ml) |
|---|---|---|
| Hydrolysate 2 of example 2 | 0.43 g | 1.08 |
| Dextrose | 4.4 g | 11 g |
| Fructose | 3.6 g | 9 g |
| Flavour apple | 0.055 g | 0.14 |
| Flavour banana | 0.037 g | 0.09 |
| Pectin[1] | 0.15 g | 0.37 |
| Water | 91.33 g | 228.36 |

[1]Genu Pectine YM-115-H CP Kelco

All dry ingredients were dissolved in water and the pH was adjusted first till pH 3.8 with citric acid (+/−0.14% on total), than till pH 3.5 with malic acid (+/−0.66% on total). The solution was preheated to 70° C. followed by addition of the pectin premix (4% in water). After homogenisation (150 bar) the product was filled and pasteurised or pasteurised and filled aseptically.

The invention claimed is:

1. A method for treatment a condition mediated by dipeptidyl peptidase IV (DPP-IV) selected from the group consisting of obesity, type 2 diabetes mellitus, and autoimmune disease, comprising administering to a subject in need thereof an effective amount of a composition comprising a protein hydrolysate enriched in peptides of 3-7 amino acids, wherein at least one said peptides is selected from the group consisting of MPLW (SEQ ID NO: 6), LPQYL (SEQ ID NO: 36), LPVPQ (SEQ ID NO:37), GPFP (SEQ ID NO: 32), PLLQ (SEQ ID NO: 33), VPYPQ (SEQ ID NO: 38), VPLGTQ (SEQ ID NO: 43), LPVPQK (SEQ ID NO: 44), KVLP (SEQ ID NO: 34), and LPL.

2. The method according to claim 1, wherein the condition mediated by DPP-IV comprises obesity, type 2 diabetes mellitus, or combinations thereof.

3. The method according to claim 2 for the treatment of obesity.

4. The method according to claim 2 for the treatment of type 2 diabetes mellitus.

5. The method according to claim 1, wherein the autoimmune disease is selected from the group consisting of rheumatoid arthritis, multiple sclerosis, and Graves' disease.

6. The method of claim 1 wherein the protein hydrolysate comprises at least one peptide comprising proline flanked by leucine on one or both sides.

7. The method of claim 1, wherein the protein hydrolysate comprises one or more peptides selected from VPYPQ (SEQ ID NO:38), VPLGTQ (SEQ ID NO:43), LPVPQK (SEQ ID NO:44), KVLP (SEQ ID NO:34) and LPL.

8. The method of claim 1 wherein the protein hydrolysate comprises 20-80 wt. % of the peptides of 3-7 amino acids.

9. The method of claim 1 wherein the protein hydrolysate comprises 30-60 wt. % of the peptides of 3-7 amino acids.

10. The method of claim 1 wherein the protein hydrolysate is a hydrolysate of casein.

* * * * *

SEQUENCE LISTING

```
<160> NUMBER OF SEQ ID NOS: 45

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys His Pro Ile Lys His Gln
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Gly Leu Pro Gln Glu Val Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Ala Pro Phe Pro Glu Val
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Val Pro Gln Leu Glu Ile
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Val Pro Leu Gly Thr Gln
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Pro Leu Trp
1

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gly Pro Ile Val Leu Asn
1               5

<210> SEQ ID NO 8
<211> LENGTH: 7
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 8

Ala Val Pro Ile Thr Pro Thr
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Ile Pro Tyr Val Arg Tyr Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Pro Phe Pro Gly Pro Ile Pro
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Gly Pro Ile Pro Asn Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Leu Pro Gln Asn Ile Pro Pro Leu
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Pro Pro Leu Thr Gln Thr
1               5
```

-continued

```
<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Leu Pro Leu Thr Gln Thr
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Val Pro Pro Phe Leu Gln
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Met Pro Phe Pro Lys Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Tyr Pro Val Glu Pro Phe
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His Leu Pro Leu Pro Leu Leu
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19
```

```
Lys Val Leu Pro Val Pro Gln Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Val Pro Tyr Pro Gln Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Pro Ile Gln Ala Phe Leu
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Pro Phe Pro Ile Ile Val
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Leu Pro Phe Leu Gly Ala
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Ile Pro Ile Gln Tyr Val
1               5

<210> SEQ ID NO 25
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 25

Phe Leu Pro Tyr Pro Tyr Tyr
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ala Pro Leu Arg Val Tyr
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Ile Pro Ala Val Phe Lys
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Leu Pro Met His Ile Arg
1               5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Pro Leu Pro
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

His Pro Ile Lys
1

<210> SEQ ID NO 31
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Pro Val Pro
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Pro Phe Pro
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Leu Leu Gln
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Val Leu Pro
1

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Pro Phe Pro Glu
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Pro Gln Tyr Leu
```

```
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Pro Val Pro Gln
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Pro Tyr Pro Gln
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Pro Phe Pro Glu Val Phe
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Met Pro Phe Pro Lys
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Gln Ser Val Leu Ser
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 42

Tyr Val Pro Glu Pro Phe
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Pro Leu Gly Thr Gln
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Pro Val Pro Gln Lys
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Thr Lys Cys Cys Thr Glu
1               5
```